US00PP36627P3

(12) United States Plant Patent
Danziger

(10) Patent No.: US PP36,627 P3
(45) Date of Patent: Apr. 22, 2025

(54) ***PETUNIA* PLANT NAMED 'DPETPW1782'**

(50) Latin Name: ***Petunia* X *hybrida***
Varietal Denomination: DPETPW1782

(71) Applicant: Gavriel Danziger, Moshav Mishmar Hashiva (IL)

(72) Inventor: Gavriel Danziger, Moshav Mishmar Hashiva (IL)

(73) Assignee: DANZIGER "DAN" FLOWER FARM, Beit Dagan (IL)

( * ) Notice: Subject to any disclaimer, the term of this patent is extended or adjusted under 35 U.S.C. 154(b) by 0 days.

(21) Appl. No.: 18/367,940

(22) Filed: Sep. 13, 2023

(65) Prior Publication Data

US 2025/0089587 P1 Mar. 13, 2025

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05); *A01H 5/02* (2013.01)

(58) Field of Classification Search
USPC ..... Plt./356.13
CPC . A01H 5/02; A01H 5/00; A01H 6/824; A01H 6/82
See application file for complete search history.

(56) References Cited

PUBLICATIONS

Canadian Food Inspection Agency for Petunia Dpetpw1782 retrieved on Aug. 30, 2024 at https://active.inspection.gc.ca/english/plaveg/pbrpov/cropreport/pet/app00013305e.shtml, one page. (Year: 2024).*
Winter, On Gardening: A lot of Hoopla about this Supertunia 2023, Texarkana Gazette retrieved online athttps://www.texarkanagazette.com/news/2023/jul/29/on-gardening-a-lot-of-hoopla-about-this-supertunia/, 5 pp. (Year: 2023).*

* cited by examiner

*Primary Examiner* — June Hwu
(74) *Attorney, Agent, or Firm* — C. Anne Whealy

(57) ABSTRACT

A new and distinct *Petunia* plant named 'DPETPW1782', characterized by its upright to outwardly spreading and mounding to eventually trailing plant habit; vigorous growth habit and rapid growth rate; freely branching habit; dense and bushy plant form; early and freely flowering habit; medium to large-sized single-type flowers that are red purple and white bi-colored; and excellent container and garden performance.

2 Drawing Sheets

Figure 1:
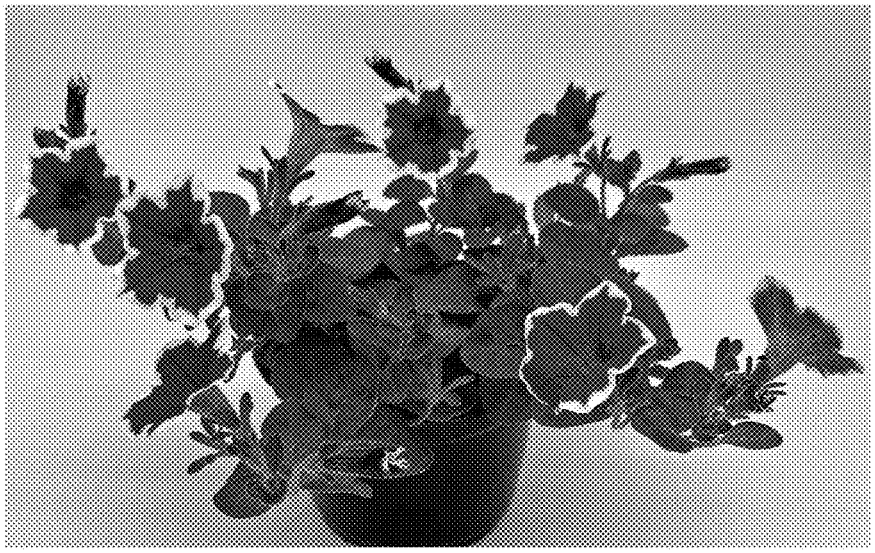

Botanical designation: *Petunia* X *hybrida.*
Cultivar denomination: 'DPETPW1782'.

BACKGROUND OF THE INVENTION

The present invention relates to a new and distinct cultivar of *Petunia* plant, botanically known as *Petunia* X *hybrida* and hereinafter referred to by the name 'DPETPW1782'.

The new *Petunia* plant is a product of a planned breeding program conducted by the Inventor in Nir zvi, Israel. The objective of the breeding program is to create new freely-branching and uniformly mounding *Petunia* plants with freely flowering habit, unique and attractive flowers and good garden performance.

The new *Petunia* plant originated from an open-pollination in November 2016 in Nir zvi, Israel of a proprietary selection of *Petunia* X *hybrida* identified as code number PEG-16-594, not patented, as the female, or seed, parent with an unknown selection of *Petunia* X *hybrida* as the male, or pollen, parent. The new *Petunia* plant was discovered and selected by the Inventor as a single flowering plant within the progeny of the stated open-pollination in a controlled greenhouse environment in Nir zvi, Israel in April 2017.

Asexual reproduction of the new *Petunia* plant by vegetative terminal cuttings in a controlled greenhouse environment in Nir zvi, Israel since May 2017 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DPETPW1782'. These characteristics in combination distinguish 'DPETPW1782' as a new and distinct *Petunia* plant:

1. Upright to outwardly spreading and mounding to eventually trailing plant habit.
2. Vigorous growth habit and rapid growth rate.
3. Freely branching habit; dense and bushy plant form.
4. Early and freely flowering habit.
5. Medium to large-sized single-type flowers that are red purple and white bi-colored.
6. Excellent container and garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more trailing than and not as upright as plants of the female parent selection.
2. Flowers of the new *Petunia* are lighter red purple in color than flowers of plants of the female parent selection.
3. Flower color pattern of plants of the new *Petunia* is more stable than flower color pattern of plants of the female parent selection.

Plants of the new *Petunia* can be compared to plants of *Petunia* X *hybrida* 'Red Carpet RIMarkable', not patented. In side-by-side comparisons, plants of the new *Petunia* differ primarily from plants of 'Red Carpet RIMarkable' in the following characteristics:

1. Plants of the new *Petunia* are denser than and not as spreading and open as plants of 'Red Carpet RIMarkable'.
2. Plants of the new *Petunia* have smaller flowers than plants of 'Red Carpet RIMarkable'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'DPETPW1782' grown in a container.

Figure 2:
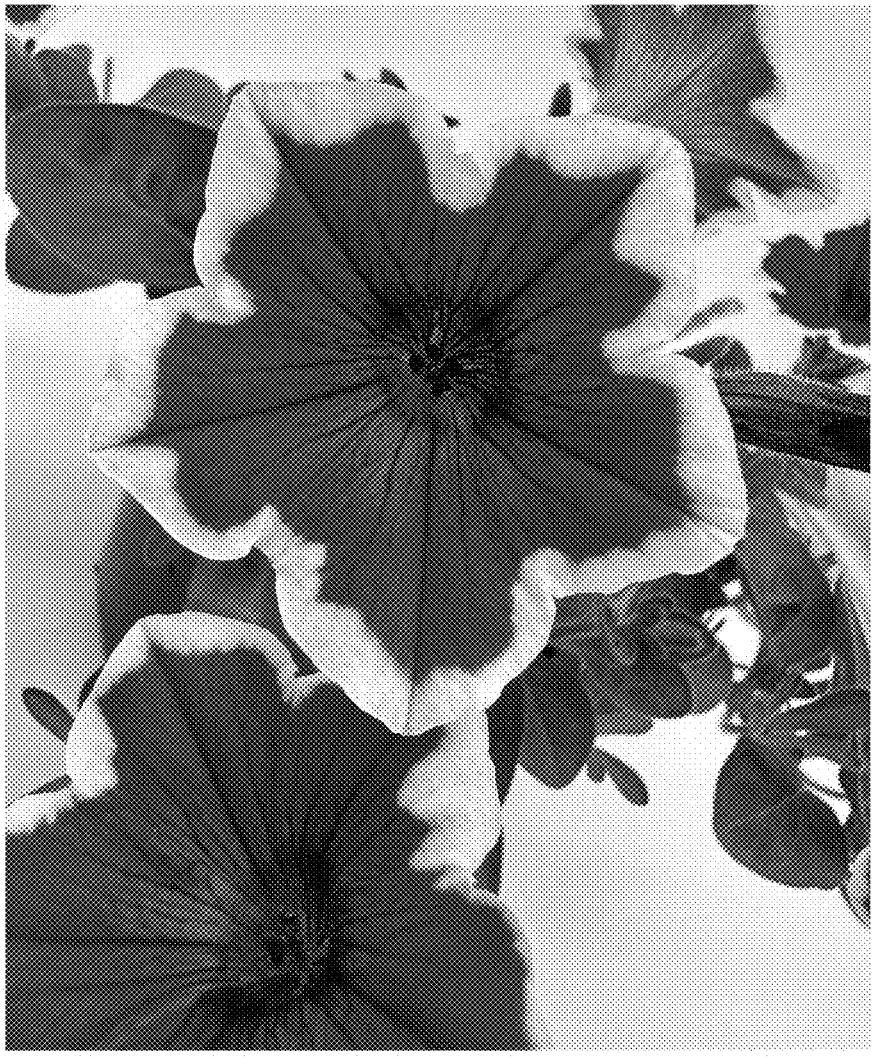

The photograph on the second sheet (FIG. 2) is a close-up view of a typical flowering plant of 'DPETPW1782'.

DETAILED BOTANICAL DESCRIPTION

The aforementioned photographs and following observations and measurements describe plants grown during the late spring in 813 ml containers in a glass-covered greenhouse in Loudon, New Hampshire and under cultural practices typical of commercial *Petunia* production. During the production of the plants, day and night temperatures averaged 20 C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'DPETPW1782'.

Parentage:

*Female, or seed, parent*.—Proprietary selection of *Petunia* X *hybrida* identified as code number PEG-16-594, not patented.

*Male, or pollen, parent*.—Unknown selection of *Petunia* X *hybrida*, not patented.

Propagation:

*Type*.—Terminal vegetative cuttings.

*Time to initiate roots, summer*.—About nine days at ambient temperatures ranging from 25 C. to 40 C.

*Time to initiate roots, winter*.—About two weeks at ambient temperatures ranging from 12 C to 25 C.

*Time to produce a rooted plant, summer*.—About 18 days at ambient temperatures ranging from 25 C to 40 C.

*Time to produce a rooted plant, winter*.—About 24 days at ambient temperatures ranging from 12 C to 25 C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; dense.

Plant description:

*Plant and growth habit*.—Upright to outwardly spreading and mounding to eventually trailing plant habit; freely branching habit with about six to eight primary lateral branches with secondary laterals developing potentially at every node, dense and bushy plant form; pinching enhances development of lateral branches; vigorous growth habit and rapid growth rate.

*Plant height*.—About 12.5 cm.

*Plant diameter* (*area of spread*).—About 28 cm by 33 cm.

*Lateral branches*.—Length: About 15 cm. Diameter: About 3 mm. Internode length: About 1.1 cm to 1.5 cm. Strength: Strong; flexible, not brittle. Aspect: Initially upright then outwardly spreading to trailing. Texture and luster: Densely pubescent; pubescence, fine; viscid; slightly glossy. Color, developing and developed: Close to 144A.

Leaf description:

*Arrangement*.—Alternate before flowering; opposite after flowers develop; leaves simple.

*Length*.—About 3.5 cm to 3.75 cm.

*Width*.—About 1.9 cm to 2.2 cm.

*Shape*.—Elliptic.

*Apex*.—Acute.

*Base*.—Cuneate.

*Margin*.—Entire, not undulate.

*Texture and luster, upper and lower surfaces*.—Moderately pubescent, pubescence, minute; viscid; matte.

*Venation pattern*.—Pinnate, arcuate.

*Color*.—Developing leaves, upper surface: Close to 147A. Developing leaves, lower surface: Close to 146A. Fully developed leaves, upper surface: Close to 147A; venation, close to 146A. Fully developed leaves, lower surface: Close to 146A; venation, close to between 144A and 146B.

*Petioles*.—Length: About 7.5 mm. Diameter: About 3 mm. Strength: Moderately strong, flexible. Texture and luster, upper and lower surfaces: Densely pubescent; slightly glossy. Color, upper and lower surfaces: Close to 144A.

Flower description:

*Flower type and flowering habit*.—Single terminal and axillary salverform flowers; flowers face mostly upward to outwardly; freely flowering habit with about 40 to 50 developing flowers and open flowers per plant.

*Natural flowering season*.—Long day responsive; long flowering period, plants flower from early spring until frost in the autumn, flowering continuous during this period; early flowering habit, plants begin flowering about six to seven weeks after planting rooted young plants.

*Flower longevity on the plant*.—Depending on temperature, about one to two weeks; petals not persistent, and sepals, persistent.

*Fragrance*.—None detected.

*Flower buds, before showing petal color*.—Length: About 1.1 cm. Diameter: About 4 mm. Shape: Oblong, elongate. Texture and luster: Pubescent; slightly glossy. Color, developing sepals: Close to between 144A and 146A.

*Flower diameter*.—About 4.75 cm to 5 cm.

*Flower depth* (*height*).—About 3.25 cm to 3.5 cm.

*Throat diameter*.—About 1.1 cm to 1.2 cm.

*Tube length*.—About 2.1 cm to 2.2 cm.

*Tube diameter, distally*.—About 1.2 cm to 1.3 cm.

*Tube diameter, proximally*.—About 4 mm.

*Petals*.—Quantity and arrangement: Five petals fused in a single salverform whorl; moderate lobing. Petal lobe length (from throat): About 2.2 cm to 2.4 cm. Petal lobe width: About 2 cm to 2.1 cm. Petal lobe shape: Roughly spatulate. Petal lobe apex: Broadly acute. Petal lobe margin: Entire; slightly undulate. Petal lobe texture and luster, upper surface: Smooth, glabrous; velvety; matte. Petal lobe texture and luster, lower surface: Smooth, glabrous with fine pubescence along the venation; matte. Throat texture and luster: Smooth, glabrous; moderately glossy. Tube texture and luster: Moderately to densely pubescent; matte. Color: When opening, upper surface: Close to 72A and towards the margins, close to NN155D. When opening, lower surface: Close to 77A to 77B and towards the margins, close to NN155D. Fully opened, upper surface: Close to 72A and towards the margins, close to NN155D; venation, same as lamina colors; with subsequent development, main color becoming closer to N87A. Fully opened, lower surface: Close to 77B and towards the margins, close to NN155D; midvein, close to 144A and lateral venation, same as lamina colors; with subsequent development, main color becoming closer to NN155D variably overlain with close to 83A to 83B. Flower throat (inside): Distally, close to 83A and proximally, close to NN155D faintly overlain with close to 144A; venation, close to 144A and N77A. Flower tube (outside): Close to 83B; venation, close to 144A and 83B to 83C; with subsequent development, color becoming closer to NN155D faintly overlain with close to 144A.

*Sepals*.—Quantity and arrangement: Five sepals fused in a single star-shaped whorl; sepals flaring outwardly. Calyx length: About 1.75 cm. Calyx diameter: About 4 cm to 5 cm. Length: About 1.75 cm. Width: About 3.5 mm to 4 mm. Shape: Linear. Apex: Obtuse to somewhat acute. Margin: Entire. Texture and luster, upper surface: Sparsely to moderately pubescent; pubescence, fine; slightly glossy. Texture and luster, lower surface: Moderately pubescent; pubescence, fine; slightly glossy. Color, upper surface: Close to 146A. Color, lower surface: Close to between 144A and 146A.

*Peduncles*.—Length: About 2 cm to 2.5 cm. Width: About 1.5 mm to 2 mm. Strength: Moderately strong to strong; wiry and flexible, not brittle. Angle: About 30 to 45 degrees from the stem axis. Texture and luster: Densely pubescent; slightly glossy. Color: Close to 144A.

*Reproductive organs*.—Stamens: Quantity per flower: About five. Filament length: About 1.75 cm. Filament color: Close to 157A to 157B. Anther length: About 2 mm. Anther shape: Bi-lobed. Anther color: Close to 79A. Pollen amount: None observed. Pistils: Quantity per flower: One. Pistil length: About 2.2 cm. Style length: About 2.1 cm. Style color: Close to 144B. Stigma diameter: About 2 mm. Stigma shape: Round to oblong. Stigma color: Close to 148A. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 1 C to about 35 C.

It is claimed:

1. A new and distinct *Petunia* plant named 'DPETPW1782' as herein illustrated and described.

* * * * *